United States Patent
Kjølhamar et al.

(10) Patent No.: US 10,767,159 B2
(45) Date of Patent: Sep. 8, 2020

(54) AUTOMATED METHOD FOR SELECTING MICROBIAL STRAINS WHICH CAN DEGRADE OR EMULSIFY OIL

(71) Applicant: EQUINOR ENERGY AS, Stavanger (NO)

(72) Inventors: Ane Kjølhamar, Trondheim (NO); Anita Skarstad, Trondheim (NO); Hans-Kristian Kotlar, Heimdal (NO)

(73) Assignee: EQUINOR ENERGY AS, Stavanger (NO)

( * ) Notice: Subject to any disclaimer, the term of this patent is extended or adjusted under 35 U.S.C. 154(b) by 111 days.

(21) Appl. No.: 15/546,771

(22) PCT Filed: Jan. 27, 2016

(86) PCT No.: PCT/NO2016/050013
§ 371 (c)(1),
(2) Date: Jul. 27, 2017

(87) PCT Pub. No.: WO2016/122333
PCT Pub. Date: Aug. 4, 2016

(65) Prior Publication Data
US 2018/0016545 A1    Jan. 18, 2018

(30) Foreign Application Priority Data
Jan. 28, 2015 (GB) .................................. 1501406.1

(51) Int. Cl.
*C12N 1/26* (2006.01)
*B01F 3/08* (2006.01)
*C09K 8/582* (2006.01)

(52) U.S. Cl.
CPC .................. *C12N 1/26* (2013.01); *B01F 3/08* (2013.01); *C09K 8/582* (2013.01)

(58) Field of Classification Search
CPC ....................................................... C12N 1/26
See application file for complete search history.

(56) References Cited

U.S. PATENT DOCUMENTS

| | | | |
|---|---|---|---|
| 2005/0106702 A1 | 5/2005 | Brigmon et al. | |
| 2010/0044031 A1 | 2/2010 | Fallon et al. | |
| 2010/0163230 A1 | 7/2010 | Kotlar | |

FOREIGN PATENT DOCUMENTS

| | | |
|---|---|---|
| CN | 102533928 | 7/2012 |
| RU | 2133770 | 7/1999 |
| RU | 2320715 | 3/2008 |
| WO | 2012/137220 | 10/2012 |

OTHER PUBLICATIONS

Bodour et al., J of Microbiological Methods, 1998, 32:273-280.*
Haines et al., J of Industrial Microbiology, 1996, 16:36-41.*
International Search Report (ISR) dated Apr. 20, 2016 in International Application No. PCT/NO2016/050013.
Written Opinion of the International Searching Authority dated Apr. 20, 2016 in International Application No. PCT/NO2016/050013.
Sandra Steinbakk, "Bioconversion of heavy oil. Characterizations of Microbial potential to bioconvert Mariner. Maureen-, Peregrino- and Bressay oil", Master thesis, Norwegian University of Science and Technology, Department of Biotechnology, pp. 13-28, May 2011.
P.F. Almeida et al., "Selection and Application of Microorganisms to Improve Oil Recovery", Engineering in Life Science, vol. 4, No. 4, pp. 319-325, 2004.
Manli Wu et al., "Degradation of polycyclic aromatic hydrocarbons by microbial consortia enriched from three soils using two different culture media", Environmental Pollution, vol. 178, pp. 152-158, Apr. 2013.
S. Ferhat et al., "Screening and preliminary characterization of biosurfactants produced by *Ochrobactrum* sp. 1C and *Brevibacterium* sp. 7G isolated from hydrocarbon-contaminated soils", International Biodeterioration & Biodegradation, vol. 65, pp. 1182-1188, Dec. 2011.
Gudiña EJ. et al., "Isolation and study of microorganisms from oil samples for application in Microbial Enhanced Oil Recovery", International biodeterioration & biodegradation, 2012, vol. 68, pp. 56-64.
Pyrchenkova I.A., et al., Applied Biochemistry and Microbiology, vol. 42, No. 3, 2006, "Selection and characterization of active psychrotrophic microbial oil-degrading microorganisms", pp. 263-269.
Jacques R.J.S., et al., Bioremediation Journal, vol. 11, No. 1, 2007, "Characterization of a polycyclic aromatic hydrocarbon— Degrading microbial consortium from a petrochemical sludge landfarming site", pp. 1-11.
Kadali K.K., et al., Journal of Microbiological Methods, vol. 88, No. 3, Mar. 2012 "A complementary approach to identifying and assessing the remediation potential of hydrocarbonoclastic bacteria.", pp. 348-355.
S.B. Petrikevich et al., Applied Biochemistry and Microbiology, vol. 39, Mo. 1, 2003, pp. 19-23.

* cited by examiner

*Primary Examiner* — Bin Shen
(74) *Attorney, Agent, or Firm* — Wenderoth, Lind & Ponack, L.L.P.

(57) ABSTRACT

The invention provides an automated method for selecting a microbial strain from within a microbial strain library which can degrade or emulsify a target oil substrate. An apparatus, device or system adapted to perform the method of the invention is further provided. The use of the method of the invention in a method for preparing a microbial inoculum suitable for use to degrade or emulsify a target oil substrate; in a method of treating an oil reservoir or environmental remediation; and in a method for producing a biosurfactant-like substance is also provided.

14 Claims, 2 Drawing Sheets a)

b)

Figure 1:
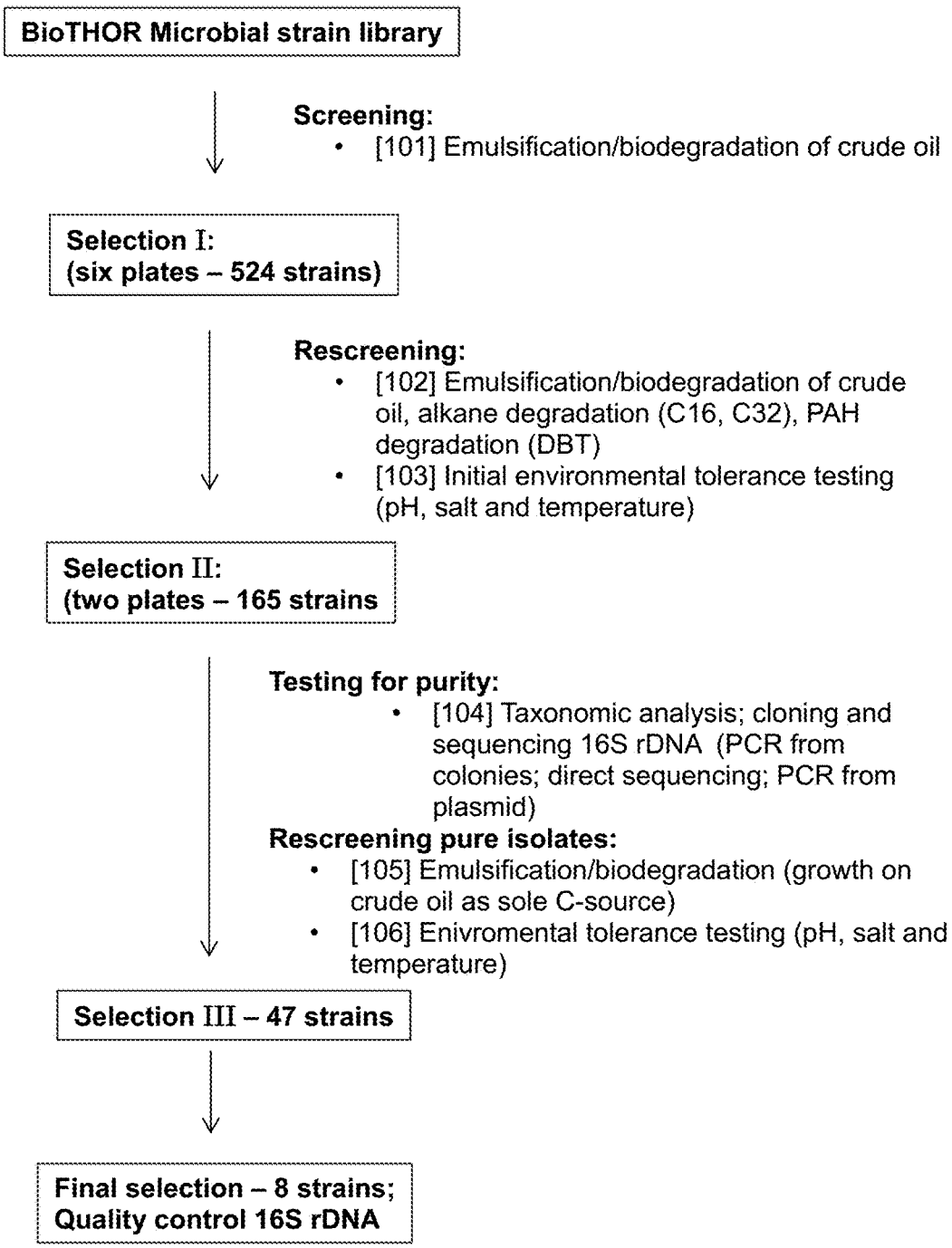

AUTOMATED METHOD FOR SELECTING MICROBIAL STRAINS WHICH CAN DEGRADE OR EMULSIFY OIL

The present invention relates generally to the identification of microbial strains from within a microbial library that are particularly suited to use in methods of enhanced oil recovery and environmental remediation, or which may produce biosurfactant-like substances of use in such methods. More specifically an automated, high-throughput, highly efficient and rapid method is provided in which particular microbial culturing steps are employed to identify microbial strains which can biodegrade or emulsify a target oil substrate, which can degrade n-alkanes and/or polycyclic aromatic hydrocarbons (PAH) and which have appropriate environmental tolerances. The invention further provides an apparatus, device or system adapted to perform the method of the invention. The invention still further provides a method for the preparation of a microbial inoculum, a method for the treatment of an oil reservoir or environmental remediation and a method for producing a biosurfactant-like substance, said methods comprising a step in which a microbial strain is identified with the automated method of the invention and then said microbial strain is used in later steps of said methods.

Much of the world's oil reserves are located below the surface of the earth in voids within bodies of reservoir rocks. In these contexts, the natural pressure of an untapped reservoir will be sufficient to drive some of the oil to the head of a bore hole introduced into the reservoir. This pressure may be provided by natural underground aquifers and/or the release of gas dissolved in the reservoir. As the volume of the oil in the reservoir is reduced the pressure drops and eventually reaches a point that is insufficient to drive oil to the surface. This is the point that primary production ceases. To achieve further recovery of oil secondary production processes are employed. Such processes involve the injection of a gas and/or a liquid into the reservoir to increase pressure in the reservoir which thereby drives oil to the surface. As the volume of oil in the reservoir is further depleted, the amount of injected fluids which return with the oil increases and eventually the process becomes uneconomical. This is the point at which secondary production ceases. After the cessation of secondary production the field may be abandoned or tertiary production techniques may be brought to bear. This may be referred to as Enhanced Oil Recovery (EOR). In other instances the reservoir rock and/or the oil which is contained therein is such that the oil is so difficult to extract that EOR techniques are applied from the outset or during secondary production.

Numerous EOR techniques are available, but the common principle embodied by each is the modification of the properties of the reservoir fluids and/or the reservoir rock characteristics in order to facilitate the movement of the oil from the reservoir to the point of collection, e.g., to the surface. Typically this involves reducing interfacial tensions between the oil and the displacing fluid and the oil and the surrounding rock interfaces, reducing oil viscosity, increasing the viscosity of the displacing fluid, creating miscible displacement, selectively plugging overly porous rock and increasing the porosity of less porous rock.

Reduction in interfacial tensions may be achieved with surfactants or alkaline chemicals which react with the organic acids in the oil to form surfactants in situ. Reducing viscosity is typically achieved by thermal means, e.g., steam flooding and in situ combustion or by dissolving gas in the oil or selectively degrading long-chain saturated hydrocarbons. Increasing the viscosity of the displacing fluid may be achieved with soluble polymers, e.g., biopolymers. Miscible displacement involves solubilising the oil in a solvent, e.g., liquid organic solvents or gases, to form a continuous homogenous phase and recovering that mixture. Selective plugging may be achieved with polymeric materials including biopolymers and microbes and rock porosity may be increased by introducing degradative chemicals, e.g., acids or alkalis, which react with the reservoir rock.

Microbial enhanced oil recovery (MEOR) defines an EOR approach which employs microbes to achieve the desired physical effects on the oil reservoir. In particular, microbes capable of producing biosurfactants may be used to produce and deliver in situ the surfactant intended to reduce interfacial tensions; microbes capable of producing solvent gases may be used to produce and deliver in situ the gases intended to solubilise the oil; microbes capable of degrading long-chain saturated hydrocarbons may be used to lower oil viscosity; acid producing microbes may be used to produce and deliver in situ the acids intended to increase porosity and/or react with the oil to create surfactants; and microbes capable of producing and delivering plugging biopolymers in situ may be used to plug overly porous rock.

It can readily be seen that the principles underlying EOR (including MEOR), i.e., recovery of hydrocarbons from a site in the natural environment, may be shared by techniques for the remediation of polluted, e.g., hydrocarbon polluted, natural and man-made environments and for the recovery of heavy hydrocarbons, e.g., oil and bitumen (asphalt), from mined hydrocarbon-impregnated sedimentary rock (so called oil- or tar-sands), which may be considered an oil reservoir in its own right and to which EOR techniques may be applied. Consequently some EOR techniques may be translated to the remediation of polluted, e.g., hydrocarbon polluted, natural and man-made environments and to the recovery of heavy hydrocarbons from mined hydrocarbon-impregnated sedimentary rock.

Environmental remediation refers to the removal or neutralisation of pollution or contaminants, e.g., hydrocarbons, from environmental media, e.g., soil, groundwater, sea water or surface water or man-made environments. Bioremediation refers to the use of organisms, e.g., microorganisms, achieve this end. Remediation technologies can be generally classified as in situ or ex situ. In situ remediation involves treating the contaminated site or location, while ex situ involves the removal of the contaminated material to be treated elsewhere.

Certain remediation techniques to address hydrocarbon contamination, e.g., oil spills, involve the application of surfactants to the hydrocarbon as a means of dispersion and to increase bioavailability. In particular is the technique of surfactant enhanced aquifer remediation (SEAR) in which surfactants are injected into the subsurface to enhance desorption and recovery of non-aqueous phase liquid. Some surfactants, especially biosurfactants, have also been observed to facilitate remediation of heavy metal, e.g., cadmium, copper, lead and zinc, contaminated sites. Other techniques involve the application of microorganisms that may consume, solubilise and/or aid the dispersion and bioavailability of the contaminants, e.g., by producing biosurfactants from hydrocarbons.

The recovery of heavy hydrocarbons from mined hydrocarbon-impregnated sedimentary rock can be achieved by the EOR techniques described above, in particular, approaches in which surfactants, e.g., biosurfactants, are used to separate heavy hydrocarbons from hydrocarbon-impregnated sedimentary rock on account of the surface activity and/or emulsifying properties of the surfactant. Another notable approach is a process termed "hot solvent extraction", a form of miscible displacement. Hot solvent extraction involves vapour injection of organic solvents into the hydrocarbon impregnated rock and as such is energy intensive. Lower temperatures may be used when a bioconverting microorganism is employed in the process as the microorganism can take advantage of the effects of the solvent on internal structure of the hydrocarbon-containing rock thereby gaining access to the interior of the rock substrate and the exerting its biosurfactant-like effects on the substrate and facilitating the separation of the hydrocarbon from the rock.

Biosurfactants are a class of structurally-diverse, highly surface-active compounds synthesised by microorganisms. These compounds are surface-active on account of having hydrophilic and hydrophobic domains and include glycolipids, phospholipids, fatty acids, lipopeptides/lipoproteins and non-lipid polymers. Biosurfactants are characterised by a lack of toxicity and susceptibility to biodegradation and so are attractive replacements for chemically synthesised surfactants that are notable for their toxicity and persistence in the environment. Indeed, the biodegradable nature of biosurfactants make them especially attractive for environmental use, e.g., in EOR and environmental remediation.

It will be seen that there is great demand for microbial strains that can function in enhanced oil recovery or environmental remediation techniques and/or that are able to produce a biosurfactant-like substance. Of course, few microbes are capable of functioning in this way and to date the identification of such microbes is laborious and time-consuming and thus costly. There is a significant need therefore for a screening method to identify such microbial strains from microbial strain libraries that is easy to perform whilst providing reliable results in a rapid and efficient manner. Methods which are sufficiently flexible to permit the selection of microbial strains that are especially suited to the conditions expected to be encountered in a target oil reservoir or site or material that is a target for environmental remediation would be particularly advantageous.

The present invention addresses these needs by providing a culture based screening method with specially adapted features that allow the rapid and efficient identification of microbial strains which can biodegrade or emulsify a target crude oil substrate, which can degrade n-alkanes and polycyclic aromatic hydrocarbons (PAH) and which have appropriate environmental tolerances.

Thus in a first aspect the invention provides an automated method for selecting a microbial strain from within a microbial strain library which can degrade or emulsify a target oil substrate, said method comprising in no particular order, unless specified:

(a) providing a plurality of receptacles adapted to receive a liquid microbial cell culture as part of a multi-well culture plate wherein the internal surface(s) of the receptacles are coated, at least in part, with a layer of the target oil substrate;

(b) applying to each receptacle a sample of one of the members of the strain library;

(c) culturing said samples in a liquid cell culture medium and monitoring the oil layer in the receptacles, wherein a change in the appearance of said layer is indicative of degradation or emulsification of said target oil substrate;

(d) selecting those samples from step (c) which caused degradation or emulsification of the oil substrate;

(e) separately culturing either (i) all the members of the library applied in step (b) or (ii) the library members selected in step (d) in the presence of an n-alkane and monitoring for degradation of said n-alkane;

(f) separately culturing either (i) all the members of the library applied in step (b) or (ii) the library members selected in step (d) in the presence of a polycyclic aromatic hydrocarbon (PAH) and monitoring for degradation of said PAH;

(g) subjecting either (i) all the members of the library applied in step (b) or (ii) the library members selected in step (d) to environmental tolerance testing, the environmental conditions tested comprising temperature, pH and ionic concentration, and optionally further comprising $O_2$ concentration or pressure;

(h) optionally repeating steps (a) to (c) with the library members selected at step (d); and (i) selecting a microbial strain on the basis of its performance in steps (c), (e), (f), (g) and optionally (h).

In a second aspect the invention provides an automated method for selecting a microbial strain from within a microbial strain library which can degrade or emulsify a target oil substrate, said method comprising in no particular order, unless specified:

(a) providing a plurality of receptacles adapted to receive a microbial cell culture wherein the internal surface(s) of the receptacles are coated, at least in part, with a layer of the target oil substrate;

(b) applying to each receptacle a sample of one of the members of the strain library;

(c) culturing said samples and monitoring the oil layer in the receptacles, wherein a change in the appearance of said layer is indicative of degradation or emulsification of said target oil substrate;

(d) selecting those samples from step (c) which caused degradation or emulsification of the oil substrate;

(e) separately culturing either (i) all the members of the library applied in step (b) or (ii) the library members selected in step (d) in the presence of an n-alkane and monitoring for degradation of said n-alkane;

(f) separately culturing either (i) all the members of the library applied in step (b) or (ii) the library members selected in step (d) in the presence of a polycyclic aromatic hydrocarbon (PAH) and monitoring for degradation of said PAH;

(g) subjecting either (i) all the members of the library applied in step (b) or (ii) the library members selected in step (d) to environmental tolerance testing, the environmental conditions tested comprising temperature, pH and ionic concentration, and optionally further comprising $O_2$ concentration or pressure;

(h) optionally repeating steps (a) to (c) with the library members selected at step (d); and (i) selecting a microbial strain on the basis of its performance in steps (c), (e), (f), (g) and optionally (h).

In this second aspect the receptacles may be culture tubes, plates (including multi-well plates, e.g., microplates), flasks or bottles. Conveniently the plurality of receptacles, or a portion thereof, are located proximally to each other during the course of the method of the second aspect of the invention. Preferably the plurality of receptacles, or a portion thereof, are in permanent contact with each other or are in a fixed spatial arrangement during the course of the method. In such embodiments the receptacles may be provided as wells of a multi-well culture plate.

The order is "specified", for example, where certain steps are performed on a selection made through performing other steps.

In certain embodiments steps (e) (i), (f) (i) or (g) (i), if performed, may be performed at any point in the method and steps (e) (ii), (f) (ii) or (g) (ii) if performed, may be performed at any point in the method following steps (a) to (d).

In preferred embodiments the method comprises steps (a) to (d) and then steps (e) (ii), (f) (ii) and (g) (iii) and optionally (h), wherein steps (e) (ii), (f) (ii) and (g) (ii) are performed in any order.

The microbial strain selected on the basis of its performance in steps (c), (e), (f), (g) and optionally (h), will be a microbial strain which caused biodegradation or emulsification of the oil substrate and optionally degradation of said n-alkane or degradation of said PAH and optionally which tolerates one or more environmental conditions selected from temperature, pH and ionic concentration, and optionally $O_2$ concentration or pressure that may be expected to be encountered during its use. Preferably the microbial strain selected on the basis of its performance in steps (c), (e), (f), (g) and optionally (h) will be a microbial strain which caused biodegradation or emulsification of the oil substrate and degradation of said n-alkane or degradation of said PAH and optionally which tolerates one or more environmental conditions selected from temperature, pH and ionic concentration, and optionally $O_2$ concentration or pressure that may be expected to be encountered during its use. Preferably the microbial strain selected on the basis of its performance in steps (c), (e), (f), (g) and optionally (h) will be a microbial strain which caused biodegradation or emulsification of the oil substrate and which tolerates one or more environmental conditions selected from temperature, pH and ionic concentration, and optionally $O_2$ concentration or pressure that may be expected to be encountered during its use and optionally which caused degradation of said n-alkane or degradation of said PAH. More preferably the microbial strain selected on the basis of its performance in steps (c), (e), (f), (g) and optionally (h) will be a microbial strain which caused biodegradation or emulsification of the oil substrate, degradation of said n-alkane or said PAH and which tolerates environmental conditions selected from temperature, pH and ionic concentration, and optionally $O_2$ concentration or pressure that expected to be encountered during its use.

In further embodiments each microbial strain of the library is scored in order of relative performance during steps (c), (e), (f), (g) and optionally (h) and selection is based on said scores. In certain embodiments greater weight is given to the score for steps (c) and optionally (h) than steps (e), (f) or (g). In certain embodiments greater weight is given to the score for steps (c), (e), (f) and optionally (h) than step (g). In still further embodiments the microbial strains of the library are ranked based on said scores and selection is of the portion of strains at the top of the rankings.

The method is automated insofar as it may be implemented without the manipulation or operation of each step by a human operator. In certain embodiments this may mean that, at least in part, preferably entirely to the extent that is practical, the method may be implemented by a computer-controlled apparatus, device or system. In view of this automation and the use of a plurality of receptacles the method may be described as high-throughput.

A library of microbial strains may be referred to as a collection of (different) microbial strains, typically each strain being represented as a taxonomically pure, or at least substantially taxonomically pure, sample of said microorganism. The samples making up the library may be obtained/ isolated directly from a natural source or from previously isolated samples. Conveniently the samples may be cultures of said microorganism.

The term "microorganism" and "microbial strain" as used herein includes any microbial organism, that is any organism that is microscopic, namely too small to be seen by the naked eye. In particular as used herein the term includes the organisms typically thought of as microorganisms, particularly bacteria, fungi, archaea, algae and protists. The term thus particularly includes organisms that are typically unicellular, but which may have the capability of organising into simple cooperative colonies or structures such as filaments, hyphae or mycelia (but not true tissues) under certain conditions. The microorganism may be prokaryotic or eukaryotic, and may be from any class, genus or species of microorganism. Examples of prokaryotic microorganisms include, but are not limited to, bacteria, including the mycoplasmas, (e.g., Gram-positive, Gram-negative bacteria or Gram test non-responsive bacteria) and archaeobacteria. Eukaryotic microorganisms include fungi, algae and others that are, or have been, classified in the taxonomic kingdom Protista or regarded as protists, and include, but are not limited to, for example, protozoa, diatoms, protophyta, and fungus-like moulds.

The plurality of receptacles of step (a) may be any number of receptacles greater than two, although typically it will be a number significantly greater than 2, e.g., greater than 5, 10, 20, 30, 40, 50, 60, 70, 80, 90 or 100. The size or shape of the receptacles is not limited except insofar as the receptacles can sustain a microbial culture (specifically, in the first aspect of the invention, a liquid microbial cell culture) for the duration of the method and have internal surfaces that will accept a coating layer of oil that may be monitored for changes in appearance.

The duration of the method may be up to 18 hrs, e.g., up to 24 or 48 hrs or 3, 4, 5, 6 or 7 days. The volume of the receptacle may therefore be greater than 50 µl, e.g., greater than 100, 200, 300, 400 or 500 µl. The depth of medium which can be placed in each receptacle may be greater than 1 mm, e.g., greater than 2, 5, or 10 mm. Many different sizes of multi-well plate (e.g., microplates) are available commercially e.g., 6, 24, 96, 384, 1536, 3456 or 9600 well plates are available. Multi-well plates of use in the invention may have an open top and a closed bottom. Said bottom may be flat with any shape, e.g., circular or polygon, preferably simple convex polygons, e.g., square, triangular, pentagon, hexagon, heptagon or octagon, more preferably simple regular polygons. In other embodiments the well bottoms are not flat, e.g., are round, conical or pyramidoidal.

Culturing of said microbial strains during the methods of the invention may be achieved in any cell culture medium (specifically, in step (c) of the first aspect of the invention, any liquid cell culture medium) suitable for the microorganism in question, e.g., lysogeny broth, DMEM, MEM, RPMI, MMAcYE (minimal medium, acetate, yeast extract), a buffered salt solution (e.g., PBS, Tris-buffered saline, HEPES-buffered saline) or a, preferably isotonic or hypertonic, salt solution (e.g., brine). It can be seen that liquid cell culture media is preferred. The medium may be supplemented with a source of carbohydrates (e.g., glucose, sucrose, molasses, corn syrup) and amino acids (e.g., beef extract, yeast extract, tryptone, peptone, casamino acids), acetate and/or other accessory compounds such as antibiotics or antifungal agents. However, preferably the medium will be a minimal medium, in that limited nutrients are present e.g., limited or no carbon source. This way the microorganisms being tested are encouraged to utilise the target oil substrate, the n-alkane or the PAH, respectively. Environmental conditions may be selected to maximise the viability of the microorganism, but in other embodiments may be conditions (e.g., temperature, pH, ionic concentration, $O_2$ concentration or pressure) that may be encountered during use. Conveniently each culture step will take place at 55-60° C. for 1-6 days based on a 20 µl volume of overnight culture inoculum.

The "oil" used in the invention is a petroleum substance. It is an oil which contains long-chain hydrocarbons, i.e., hydrocarbons of 10 or more carbon atoms, e.g., 10, 15, 20 or 25 or more carbon atoms. The oil may be a heavy oil, a light oil or an oil of intermediate weight. Heavy oil may be considered as an oil which has an API gravity of less than 20°. Light oil may be considered as an oil which has an API gravity of greater than 30°. In certain embodiments the oil used is a crude oil, i.e., petroleum in its natural form. It may therefore be light crude oil, heavy crude oil (including bitumen/asphalt), or a crude oil of intermediate weight. Advantageously, the oil used will be an oil obtained from a target oil reservoir or a site or material that is a target for environmental remediation. In other embodiments the oil is a product which has been refined from crude oil, e.g., an oil which is, or which contains, a crude oil fraction.

The target oil substrate is provided as a layer on at least part of the inner surfaces of the receptacle, in particular a part of the inner surfaces of the receptacle that will be in contact with the culture media or the microorganisms during the course of the method. Conveniently, the oil coating will be entirely below the surface level of the culture media, e.g., at the bottom of the receptacle (as defined by the normal orientation of the receptacle). In other embodiments the oil layer covers essentially the entire inner surface of the receptacle. The method may include a step of applying said layer of target oil substrate to said receptacles, e.g., in a volatile solvent compatible with the inner surface of the receptacle receiving the oil layer; the volatile solvent may be lost by evaporation to leave the oil layer as a coating on the receptacle.

Degradation or emulsification of the target oil substrate is indicated by a change in the appearance of the layer of target oil substrate in the receptacle. This may be monitored over the course of the method manually by a human operator with or without computer-assisted means, e.g., (computer-controlled) turbidity measurements or image capture and analysis. More conveniently the method may be automated through the use of said computer-assisted means. Such computer-assisted methods may be quantitative or semi-quantitative. In preferred embodiments the changes in appearance are assessed a number of times over the course of the method and a rate of change is determined. This may be quantitative, semi-quantitative or, when in comparison to the rate of change of the other members of the library being tested concurrently, qualitative.

In certain embodiments step (c) is performed in a minimal medium in which the target oil substrate is the only significant carbon source available. In these embodiments an expansion in the number of microorganisms in the culture, i.e., the growth of the colony, can also be taken as an indication of degradation of the target oil substrate because the microorganisms must be breaking down the target oil substrate to use as a nutrient source. Conveniently live cell number in a liquid culture may be measured by $OD_{600}$ measurements. Other techniques are available, for example those which exploit the characteristic loss of cell membrane integrity in dead microorganisms. Membrane impermeable dyes (e.g., trypan blue and propidium iodide) are routinely used to assess membrane integrity. These dyes are excluded from intact microorganisms and so no staining occurs in such microorganisms. If cell membrane integrity is compromised, these dyes can access the microorganism and stain intracellular components. Alternatively, or in addition, dyes that only stain microorganisms with intact membranes are used to give an indication of the viability of the cell. The Live/Dead® BacLight® Assay of Invitrogen® Ltd is an assay that uses two dyes, one to stain dead cells, the other to stain live cells. Another approach to assessing membrane integrity is to detect the release of cellular components into the culture media, e.g., lactate dehydrogenase, or the characteristic morphology of dead cells. In the context of these techniques differentiation between live and dead cells is usually made by monitoring the cultures by microscope or by a cell sorting device, e.g., a flowcytometer.

In preferred embodiments step (e) comprises (e1) providing a plurality of receptacles adapted to receive a microbial cell culture, e.g., those described above;

(e2) applying to each receptacle either (i) all the members of the library applied in step (b) or (ii) the library members selected in step (d);

(e3) culturing said library members in the presence of an n-alkane and monitoring for degradation of said n-alkane.

The identity of the n-alkane is not limited, although typically it will be a substantially non-volatile n-alkane under the culture conditions used. The n-alkane will typically be at least a $C_6$ alkane, e.g., at least a $C_8$, $C_{10}$, $C_{12}$, $C_{14}$, $C_{16}$, $C_{18}$, $C_{20}$, $C_{22}$, $C_{24}$, $C_{26}$, $C_{28}$, $C_{30}$, $C_{32}$, $C_{34}$, $C_{36}$, $C_{38}$ or $C_{40}$ alkane The n-alkane may be straight or branched. In preferred embodiments the n-alkane is a compound that may be expected to be encountered by the selected microbial strain during use. A plurality of n-alkanes may be applied, e.g., two or more of a $C_8$, $C_{10}$, $C_{12}$, $C_{14}$, $C_{16}$, $C_{18}$, $C_{20}$ $C_{22}$, $C_{24}$, $C_{26}$, $C_{28}$, $C_{30}$, $C_{32}$, $C_{34}$, $C_{36}$, $C_{38}$, or $C_{40}$ alkane or an alkane with a intervening number of carbons. The n-alkane may be applied as a combination of alkanes e.g., a combination of alkanes comprising alkanes ranging from any of $C_8$, $C_{10}$, $C_{12}$, $C_{14}$, $C_{16}$, $C_{18}$, or $C_{20}$ alkanes to $C_{22}$, $C_{24}$, $C_{26}$, $C_{28}$, $C_{30}$, $C_{32}$, $C_{34}$, $C_{36}$, $C_{38}$, or $C_{40}$ alkanes.

Alkane degradation may be detected by any convenient means, the detection method may be direct or indirect. Such means include following the generation of formazan dyes from tetrazolium salts. Representative examples of tetrazolium salts include INT (2-(4-iodophenyl)-3-(4-nitrophenyl)-5-phenyl-2H-tetrazolium chloride), MTT (3-(4,5-dimethyl-2-thiazolyl)-2, 5-diphenyl-2H-tetrazolium bromide), XTT (2,3-bis-(2-methoxy-4-nitro-5-sulfophenyl)-2H-tetrazolium-5-carboxanilide), MTS (3-(4,5-dimethylthiazol-2-yl)-5-(3-carboxymethoxyphenyl)-2-(4-sulfophenyl)-2H-tetrazolium), TTC (2,3,5-triphenyl-2H-tetrazolium chloride) and NBT (nitroblue tetrazolium).

In preferred embodiments step (f) comprises (f1) providing a plurality of receptacles adapted to receive a microbial cell culture, e.g., those described above;

(f2) applying to each receptacle either (i) all the members of the library applied in step (b) or (ii) the library members selected in step (d);

(f3) culturing said library members in the presence of a PAH and monitoring for degradation of said PAH.

In accordance with the invention the term "polycyclic aromatic hydrocarbon" extends to heterocyclic PAH analogues, i.e., PAHs carrying one or more, e.g., up to 1, 2, 3, 4, 5 or 6 heteroatoms, e.g., nitrogen, sulphur, oxygen and/or phosphorous atoms. The term further extends to alkyl substituted forms of PAHs and heterocyclic PAH analogues, e.g., PAHs and heterocyclic PAH analogues carrying one or more, e.g., up to 1, 2, 3, 4, 5 or 6 alkyl groups. Substituting alkyl groups may be of any size, e.g., up to 10, 8, 6, 4 or 2 carbon atoms and may be branched or linear.

The identity of the PAH is not limited and may be selected from 2 ringed PAHs (e.g., azulene, naphthalene, 1-methylnaphthalene, sapotalin), 3 ringed PAHs (e.g., acenaphthene, acenaphthylene, anthracene, fluorene, phenalene, phenanthrene), 4 ringed PAHs (e.g., benz[a]anthracene, benzo[a]fluorine, benzo[c]phenanthrene, chrysene, fluoranthene, pyrene, tetracene, triphenylene, tricyclobutabenzene), 5 ringed PAHs (e.g., benz[e]acephenanthrylene, benzopyrene, benzo[a]pyrene, benzo[e]pyrene, benzo[a]fluoranthene, benzo[b]fluoranthene, benzo[j]fluoranthene, benzo[k]fluoranthene, corannulene, dibenz[a,h]anthracene, dibenz[a,j]anthracene, olympicene, pentacene, perylene, picene, tetraphenylene), or 6 or more ringed PAHs (e.g., anthanthrene, benzo[ghi]perylene, dicoronylene, coronene, diindenoperylene, helicene, heptacene, hexacene, kekulene, ovalene, zethrene) and heterocylic analogues and alkyl substituted derivatives thereof. Dibenzothiophene and carbazole are specific examples of heterocyclic PAH analogues.

PAH degradation may be monitored by any convenient means, for instance the degradation products or intermediates may be detectable by virtue of the wavelengths of light which they absorb. This may result from the conjugated double bounds arising from splitting the ring structures. If absorbance is in the visual range a colour change may be observed, for instance degradation of dibenzothiophene results in a deep purple product which is easy to measure or inspect visually.

Environmental tolerance testing may comprise culturing the microbial strains under varying temperatures, pH levels and ionic concentration, and optionally $O_2$ concentrations and pressures and determining the limits of these conditions at which colony viability ceases. In certain embodiments this may involve culturing the microbial strains at two or more, e.g., 3, 4 or 5 or more different values for each condition (temperature, pH, ionic concentration and optionally $O_2$ concentration or pressure). By comparing colony viability at the different values used environmental tolerances may be determined. In other embodiments environmental testing may comprise determining the above mentioned conditions present in a target oil reservoir or site or material that is a target for environmental remediation and culturing the microbial stains under the conditions so determined in order to confirm tolerance to such conditions. In certain embodiments colony viability may be measured as death of the colony, e.g., the point at which 50%, 75% or 90% of the colony cells are dead. In other embodiments this may be measured as the point at which the growth in the number of cells in the colony ceases. Conveniently live (intact) cell number in a liquid culture may be measured as described above. In further embodiments the optimum environmental conditions are determined by measuring the rate of colony growth under varying temperatures, pH levels and ionic concentration, and optionally $O_2$ concentrations and pressures.

Environmental tolerance testing may take place in any cell culture medium suitable for the microorganism in question, e.g., those recited above, in particular the liquid cell culture media recited above. The medium may be supplemented with a source of carbohydrates (e.g., glucose, sucrose, molasses, corn syrup), acetate and amino acids (e.g., beef extract, yeast extract, tryptone, peptone, casamino acids) and/or other accessory compounds such as antibiotics or antifungal agents. However, in certain embodiments the medium will be a minimal medium, in that limited nutrients are present, supplemented with the target oil substrate, the n-alkane and/or the PAH. In this way the environmental tolerance of the microbial strains under conditions that may be encountered during use are tested more directly.

By including environmental testing in the method of the invention a screening method is provided that has the ability to identify and select microbial strains that not only degrade or emulsify a target oil substrate, but which may do so under environmental conditions they are expected to encounter during a proposed use. As discussed above, such uses include enhanced oil recovery and environmental remediation. Thus, in preferred embodiments the environmental testing will include conditions representative of, which mimic, or which correspond to, a target oil reservoir or site or material in need of remediation.

In the context of subterranean oil reservoirs such conditions may be a pH of 5-10, a temperature of 0-150° C. and a salt concentration of up to 30% w/v, and e.g., a pressure of up to 300 bar and substantially anaerobic. In certain embodiments microbial strains will be selected to tolerate such conditions.

As such, in certain embodiments of the method of the invention during step (g) the microbial strains will undergo culture at pHs of 5 to 10, e.g., 6-9, 7-9, 7-8 or about pH 7.0 (e.g., pH 6.5-7.5, pH 6.8-7.2 or pH 6.9-7.1). In other embodiments of the method of the invention during step (g) the microbial strains will undergo culture at temperatures of 0-150° C., e.g., 20-120° C., 50-100° C., 50-90° C., 50-85° C., 50-80° C., 50-70° C., 50-65° C., 50-60° C., 55-80° C., 55-70° C., 55-65° C., 55-60° C., 60-65° C., 60-70° C., 60-80° C., 65-70° C., 65-75° C., 65-80° C., 65-85° C. In other embodiments of the method of the invention during step (g) the microbial strains will undergo culture at salt concentrations of up to 30% w/v, e.g., up to 20%, 15%, 10%, 8%, 6%, 4%, 3%, 2% or 1% w/v. In other embodiments of the method of the invention during step (g) the microbial strains will undergo culture at pressures of up to 300 bar, e.g., up to 200 bar, 150 bar, 100 bar, 80 bar, 60 bar, 40 bar or 20 bar. In other embodiments of the method of the invention during step (g) the microbial strains will undergo culture at anaerobic or microaerophilic conditions.

In preferred embodiments step (g) comprises (g1) providing a plurality of receptacles adapted to receive a microbial cell culture, e.g., those described above;

(g2) applying to each receptacle either (i) all the members of the library applied in step (b) or (ii) the library members selected in step (d);

(g3) culturing said library members under various environmental conditions described herein and monitoring said library members for tolerance to said conditions.

In further embodiments steps (c), (e) and/or (f) are each preceded by a step in which said library members to be cultured are exposed to, i.e., precultured with, the target oil substrate, the n-alkane or the PAH, respectively. In this way library members which can be induced to degrade or emulsify the target oil substrate, or to degrade the n-alkane or to degrade the PAH may be identified. Typically this preculturing step may be an overnight culture of the library members and it is a sample of this pre- (overnight) culture that is cultured in steps (c), (e) and/or (f).

In further embodiments the method of the invention comprises repeating steps (a)-(c), (e), (f) and/or (g), e.g., (a)-(g) and preferably (a)-(c), prior to step (i) and the step of selecting a microbial strain is based on its performance in steps (c), (e), (f), (g) and optionally (h) and any of steps (c), (e), (f), (g) which have been repeated.

In a further aspect the invention provides an apparatus, device or system adapted to perform a method as defined herein, preferably comprising a computer programmed to control at least part of said methods, e.g., the culturing steps, the monitoring steps and/or the sample handling steps.

As already discussed herein the screening method of the invention is a method to identify microorganisms which can degrade or emulsify a target oil substrate, which may degrade n-alkanes and/or polycyclic aromatic hydrocarbons (PAH) and which may have appropriate environmental tolerances for use in enhanced oil recovery from a target oil reservoir or in an environmental remediation procedure at a target site or material undergoing environmental remediation.

The invention therefore further provides a method for preparing a microbial inoculum suitable for use to degrade or emulsify a target oil substrate, said method comprising (i) performing the automated method of the invention as described herein, (ii) culturing a sample of said selected strain to increase the numbers of cells in the culture.

The skilled person would be able to design suitable culture conditions for his/her needs, in particular taking the results of the environmental tolerance tests into consideration.

The inventors have found that achieving a cell density of $5 \times 10^8$ cells/ml to $5 \times 10^9$ cells/ml, e.g., $6 \times 10^8$ to $2 \times 10^9$ cells/ml, $7 \times 10^8$ to $9 \times 10^8$ cells/ml or about $8 \times 10^8$ cells/ml prior to use may be advantageous. It may also be advantageous to use the selected microorganism, e.g., at these cell densities, when the cells are in the exponential phase, preferably late exponential phase, of their growth curve. Harvesting at these densities and timepoints is thought to provide cells with the maximum capacity to utilise oil (e.g., maximum amount of cells and maximum viability). Similarly, in certain embodiments cells in the stationary phase of their growth curve are not used.

The culture medium used may be any medium suitable for culturing the selected microorganism, e.g., lysogeny broth, DMEM, MEM, RPMI, and MMAcYE, supplemented with a source of carbohydrates (e.g., glucose, sucrose, molasses, corn syrup), amino acids (e.g., beef extract, yeast extract, tryptone, peptone, casamino acids) or acetate. It can be seen that liquid cell culture media is preferred.

Preferably the pH of the culture will be maintained at pH 5-10, e.g., 6-9, 7-9, 7-8 or about pH 7.0 (e.g., pH 6.5-7.5, pH 6.8-7.2 or pH 6.9-7.1). Fluctuations outside of the preferred ranges may be tolerated, but for most of the culture period the pH will be at or within preferred range endpoints.

Preferably the temperature of the culture will be maintained at 20-100° C., e.g., 25-90° C., 35-85° C., 40-80° C., 45-60° C., 45-65° C., 45-70° C., 45-80° C., 50-60° C., 50-65° C., 50-70° C., 50-75° C., 50-80° C., 55-60° C., 55-65° C., 55-70° C., 55-75° C., 55-80° C. preferably 55-60° C. Fluctuations outside of the preferred ranges may be tolerated, but for most of the culture period the temperature will be at or within preferred range endpoints.

Preferably the salt concentration of the culture will be maintained at or below 30% w/v, e.g., at or below 20%, 15%, 10% 8%, 6%, 4%, 3%, 2% or 1% w/v. In certain embodiments the salt concentration in the culture may be negligible to 0% w/v.

The selected microorganism may be cultured aerobically, anaerobically or in a regime having one or more periods of aerobic culture and one or more periods of anaerobic culture.

Culturing may take place in any suitable vessel adapted for large-scale cultures. In preferred embodiments a bioreactor (a system for the growth of cells in culture), preferably of industrial scale, may be used, preferably under the conditions described herein. Suitable bioreactors are available in the art and the skilled person would find such reactors routine to use. Bioreactors may be specially designed to supply nutrients to a living culture of the selected microorganism under optimum conditions and/or facilitate the removal of products produced by the cells, e.g., waste products that may inhibit growth. The bioreactor may be adapted to function in a batch-wise fashion or as a continuous culture, or both.

Exposing the microorganisms of the inoculum to the target oil is expected to ensure the microorganisms are able to begin metabolising oil in situ in the quickest time. It may be advantageous to expose the microorganisms of the inoculum to the target oil before the target cell density/growth phase is reached. Amounts of target oil which may be included in the culture media may be varied, but 0.01-0.5% w/v, e.g., 0.02-0.4%, 0.05-0.3%, 0.08-0.2%, or about 0.1% w/v, may be sufficient.

The inoculum may be provided (and used) as a direct product of the culturing step. In other embodiments the microorganisms are isolated from the rest of the culture and provided in a convenient physical form. Within such forms the microorganisms may be dormant (e.g., in spore form), stationary or growing. For instance, the microorganisms may be provided as a suspension of cells or a pellet of cells in a liquid acceptable to said microorganisms, e.g., water, a culture medium (e.g., lysogeny broth, DMEM, MEM, RPMI, MMAcYE (minimal medium, acetate, yeast extract)) a buffer (e.g., PBS, Tris-buffered saline, HEPES-buffered saline) or a, preferably isotonic or hypertonic, salt solution (e.g., brine). In certain embodiments the liquid is a liquid suitable for cryopreservation (e.g., a cryoprotectant), for instance, glycerol and/or DMSO. The microorganisms may also be provided in dried form, e.g., lyophilised. In such embodiments the microorganisms may be present together with one or more lyophilisation excipients, e.g., salts (organic and inorganic), amino acids and carbohydrates (mono-, di-, oligo- and polysaccharides).

The inoculum of the invention may be provided with further components, in particular, components to facilitate the use of the microorganisms (e.g., growth media, oil reservoir delivery vehicles, essential nutrients and growth supplements) and/or components of use alongside the microorganism in enhanced oil recovery and environmental remediation (e.g., EOR chemicals, oil well treatment chemicals and remediation chemicals). In these latter embodiments the inoculum may be described as an MEOR composition and/or a bioremediation composition.

It may be advantageous in certain instances to use a plurality of microbial strains in combination to degrade or emulsify a target oil substrate in an enhanced oil recovery or environmental remediation application. Combinations of different microbial strains and relative proportions thereof may provide an inoculum with a more elaborate set of properties that are more precisely suited to particular contexts. Thus, the inoculum of the invention may comprise more than one microbial strain.

In a further aspect the invention provides a method of treating an oil reservoir or environmental remediation, said method comprising (i) performing the automated method of the invention or the method for preparing a microbial inoculum as described herein, (ii) introducing a sample of said selected microbial strain or said microbial inoculum to an oil reservoir or contacting a site or material undergoing environmental remediation with a sample of said selected microbial strain or said microbial inoculum.

In accordance with the invention the generality of the term "oil reservoir" is taken to extend to hydrocarbon-impregnated sedimentary rock, in particular hydrocarbon-impregnated sedimentary rock that has been mined from the earth, i.e. hydrocarbon-impregnated sedimentary rock that has been isolated from its natural environment or which may be described as being ex situ, unless specific context dictates otherwise. Introduction of the microbial strain or said microbial inoculum to such reservoirs may be viewed as contacting said microbial strain or said microbial inoculum with hydrocarbon-impregnated sedimentary rock, especially mined hydrocarbon-impregnated sedimentary rock. In other specific embodiments the reservoir is a subterranean reservoir. Treatment of the reservoir preferably results in enhanced oil recovery from the reservoir.

The type of oil which may be present in the reservoir is not limited. The oil may be a light oil, a heavy oil (including bitumen/asphalt), or an oil of intermediate weight.

The oil reservoir may be a subterranean oil reservoir which has undergone a secondary stage of oil recovery. By "undergone a secondary stage of oil recovery" it is meant that artificial means, e.g., injection of a gas and/or a liquid into the reservoir, have been employed to increase pressure in the reservoir in order to drive oil to the surface. In certain embodiments such techniques have reached the point of economic non-viability. In other embodiments the oil reservoir may still be in a secondary stage of oil recovery, e.g., at the stage of displacement fluid break through, or prior to displacement fluid break through.

Sites or locations which may be in need to bioremediation are not restricted, although typically such sites or locations include, but are not limited to, groundwater, aquifers, surface water courses, subsurface water courses, soil, earth and coastal and marine environments. Artificial (i.e., man-made) sites and locations may also in be included, e.g., buildings (domestic and industrial) intact, demolished or otherwise and their foundations, refuse dumps (domestic and industrial), transport infrastructure and so on. A material in need or bioremediation is a material present at or taken from such sites or locations.

The contaminant(s) at the site or location or a material in need of bioremediation is also not restricted, but the properties of the microbial strain or said microbial inoculum as determined by the method of the invention are believed to make them especially suited to the remediation of hydrocarbon (e.g., crude oil, refined petroleum products, PAHs and alkanes) and/or heavy metal contamination.

In a further aspect the invention provides the use of one or more selected microbial strains or the microbial inoculum in a method of enhanced oil recovery or a method of environmental remediation.

In a further aspect the invention provides a method for producing a biosurfactant-like substance, said method comprising (i) performing the automated method of the invention as described herein and selecting a strain which can emulsify the target oil substrate, (ii) culturing a sample of said selected strain under conditions which result in BLS production.

Conditions which result in BLS production will typically include the presence of a hydrocarbon source, e.g., an oil (e.g., crude oil) or in certain instances alkanes and/or polycyclic aromatic hydrocarbons. In preferred embodiments the hydrocarbon source will be the target oil of the selection steps. After culturing the BLS is present in the supernatant and may be harvested.

Combinations of the selected strains of the invention may be used in these aspects of the invention to produce a BLS. In doing so more a complex BLS may be prepared which has particular and advantageous properties. The selected combination may be cultured together or may be cultured separately. The method of producing a BLS of the invention may therefore comprise a step in which a supernatants from a plurality of different microbial cultures, or one or more fractions thereof, are combined to produce a BLS. The relative proportions of each strain cultured together, or the relative proportions of the culture extracts in the combination BLS, may be same or different. By varying the proportions as well as the identity of strains/culture extracts greater control over the proprieties of the BLS may be achieved.

In a further aspect there is provided a biosurfactant-like substance, wherein said substance is obtained or obtainable from the methods described herein.

A "biosurfactant" is a biological (i.e., produced by microbes, e.g., bacteria, yeasts or fungi) surface active agent which lowers the surface tension and interfacial energy of water, with oil-water emulsifying activity. A "biosurfactant-like substance" as used herein is a biological substance, produced from microbes, that shares these functional features. It is a substance that may not have been characterised down to its individual molecular constituents but typically contains a mixture of compounds which together and/or individually provide surfactant functionality, e.g., proteins or peptides, fatty acids (e.g., palmitic acid), phalates (di-isononyl phthalate), etc. The substance will typically also contain one or more non-biosurfactant compounds, e.g., water.

More specifically the BLS of the invention will have emulsifying activity, surface/interfacial activity and/or oil displacement activity against at least one hydrocarbon (preferably crude oil) substrate. Preferably the BLS of the invention will show effects in one or more of the following tests, as detailed in the Examples: oil displacement assay, emulsification capacity index, shake flask test, hydrocarbon emulsification test and drop collapse test.

Culturing of the selected strain takes place in a suitable cell culture medium. The identity of the medium is not restricted except insofar as it is suitable for the culture of the selected microbial strain. Such media include, but are not limited to lysogeny broth, DMEM, MEM, RPMI and MMA-cYE supplemented with a source of carbohydrates (e.g., glucose, sucrose, molasses, corn syrup), amino acids (e.g., beef extract, yeast extract, tryptone, peptone casamino acids) or acetate. It can be seen that liquid cell culture media is preferred.

Preferably the pH of the culture will be maintained at pH 5-10, e.g., 6-9, 7-9, 7-8 or about pH 7.0 (e.g., pH 6.5-7.5, pH 6.8-7.2 or pH 6.9-7.1). Fluctuations outside of the preferred ranges may be tolerated, but for most of the culture period the pH will be at or within preferred range endpoints.

Preferably the temperature of the culture will be maintained at 20-100° C., e.g., 25-90° C., 35-85° C., 40-80° C., 45-60° C., 45-65° C., 45-70° C., 45-80° C., 50-60° C., 50-65° C., 50-70° C., 50-75° C., 50-80° C., 55-60° C., 55-65° C., 55-70° C., 55-75° C., 55-80° C. preferably 55-60° C. Fluctuations outside of the preferred ranges may be tolerated, but for most of the culture period the temperature will be at or within preferred range endpoints.

Preferably the salt concentration of the culture will be maintained at or below 30% w/v, e.g., at or below 20%, 15%, 10%, 8%, 6%, 4%, 3%, 2% or 1% w/v. In certain embodiments the salt concentration in the culture may be negligible to 0% w/v.

The selected microorganism may be cultured aerobically, anaerobically or in a regime having one or more periods of aerobic culture and one or more periods of anaerobic culture.

In these embodiments relating to the preparation of BLS, it may also be advantageous to culture the selected strain to a cell density of $5 \times 10^8$ cells/ml to $5 \times 10^9$ cells/ml, e.g., $6 \times 10^8$ to $2 \times 10^9$ cells/ml, $7 \times 10^8$ to $9 \times 10^8$ cells/ml or about $8 \times 10^8$ cells/ml before harvesting. It may also be advantageous to allow the culture to continue at the above cell densities for a period of time prior to harvesting, i.e., to allow the culture to continue for period of time in the stationary phase of its growth curve. The optimum incubation time may be determined by the skilled person without undue burden but it may be at least 6, 12 or 24 hours, e.g., at least 1, 2, 5 or 10 days.

Suitable hydrocarbon sources may be oil, e.g., crude or partially refined oil, highly or partially fractionated petroleum products (e.g., petrol, diesel, kerosene, purified alkanes, PAHs) or materials (e.g., soil, water, refuse) contaminated with the same. As can be seen, the type of oil which may be used as a hydrocarbon source is not limited. The oil may be light crude oil, heavy crude oil, or an oil of intermediate weight. Amounts of hydrocarbon which may be included in the culture media may be varied, but 0.01-0.5% w/v, e.g., 0.02-0.4%, 0.05-0.3%, 0.08-0.2%, or about 0.1% w/v, may be sufficient.

The culturing of the selected strains in the production methods of the invention may take place in any suitable vessel. In preferred embodiments a bioreactor (a system for the growth of cells in culture), preferably of industrial scale, may be used, preferably under the above described conditions. Suitable bioreactors are available in the art and the skilled person would find such reactors routine to use. Bioreactors may be specially designed to supply nutrients to a living culture under optimum conditions and/or facilitate the removal of products produced by the cells, e.g., waste products that may inhibit growth or BLS production, and/or the BLS containing culture medium. The bioreactor may be adapted to function in a batch-wise fashion or as a continuous culture, or both.

In preferred embodiments the BLS is the extracellular medium (supernatant) of the culture and is substantially free of microbial cells and/or cell debris. Cells and/or cell debris can be removed, e.g., by filtration, chromatography, centrifugation and/or gravitational separation. The production method of the invention therefore may include at least one fractionation step, e.g., a step(s) of filtration, chromatography, centrifugation and/or gravitational separation, to remove at least a portion of the intact cells and/or cell debris from the culture. Filtration, centrifugation and/or gravitational separation are preferred for their convenience. The BLS may be described as cell-free, or at least substantially cell-free, when all, or at least substantially all, intact cells are removed, i.e., fewer than 1000 cells/ml, e.g., fewer than 500, 100, 50 or 10 cells/ml, are present. Free, or at least substantially free, of cell debris means less than 1%, e.g., less than 0.5%, 0.1%, 0.05%, or 0.01%, of the volume of the composition is cell debris.

Alternatively, a product may comprise the BLS and the selected microorganisms which generated it.

In still further embodiments the BLS is a concentrated form of the above preparations, i.e., a portion of the water and/or a non-surfactant fraction has been removed from the fractionated products. This may be by chromatography (e.g., size exclusion, ion exchange, HPLC, hydrophobic interaction chromatography), dialysis, filtration (e.g., ultrafiltration and nanofiltration), precipitation (e.g., with alcohol, e.g. methanol or isopropanol), distillation or evaporation. The production method of the invention therefore may further include at least one concentrating step, e.g., a step(s) of chromatography (e.g., size exclusion, ion exchange, HPLC, hydrophobic interaction chromatography) dialysis, filtration (e.g., ultrafiltration and nanofiltration), precipitation, distillation or evaporation that removes a portion of the water and/or non-surfactant component(s) from the surfactant component(s) or vice versa.

A BLS as produced in accordance with the invention may be provided in any convenient form. Liquid forms, e.g., aqueous or organic or a mixture of both, or dried forms, e.g., lyophilised forms, are specifically contemplated. A BLS may be formulated into a composition also comprising additives, e.g., preservatives, stabilisers, antioxidants or colourings. Lyophilised forms may comprise one or more lyophilisation excipients, e.g., salts (organic and inorganic), amino acids and carbohydrates (mono-, di-, oligo- and polysaccharides). Other additives include components of use in methods of EOR, e.g., MEOR, and environmental remediation, e.g., bioremediation, including oil well delivery vehicles, oil well treatment chemicals and remediation chemicals. The above discussion of such components applies mutatis mutandis to these embodiments.

As discussed above, the use of chemically synthesised surfactants and biosurfactants in methods of EOR have been proposed. Thus, in a further aspect there is provided a method of EOR, said method comprising performing the method for producing a BLS of the invention described herein and then introducing the BLS so produced to an oil reservoir.

As discussed above, the use of chemically synthesised surfactants and biosurfactants in methods of environmental remediation have been proposed. Thus in a further aspect there is provided a method of environmental remediation, said method comprising performing the method for producing a BLS of the invention described herein and then contacting a BLS of the invention with a site or a material in need of environmental remediation.

Preferred methods of environmental remediation and of sites or materials which may be in need of environmental remediation may be the same as described above in connection with environmental remediation methods of the invention utilising microorganisms.

In a further aspect the invention provides the use of a BLS produced in accordance with the invention in a method of EOR or a method of environmental remediation.

Chemically synthesised surfactants have numerous industrial, domestic, agricultural, food science, medical and cosmetic applications, e.g., as emulsifying agents, hydrophilising agents, wetting agents, dewatering agents, dispersion agents and antimicrobial agents. The uses of a BLS produced in accordance with the invention in such fields and as such agents constitute further aspects of the invention.

The invention will now be described by way of non-limiting Examples with reference to the following figures in which:

FIG. 1 shows a flow chart summarising one detailed embodiment of the method of the invention. According to the flow chart [101] is "Emulsification/biodegradation of crude oil"; [102] is "Emulsification/biodegradation of crude oil, alkane degradation (C16, C32), PAH degradation (DBT)"; [103] is "Initial environmental tolerance testing (pH, salt and temperature)"; [104] is "Taxonomic analysis; cloning and sequencing 16S rDNA (PCR from colonies;

direct sequencing; PCR from plasmid)"; [105] is "Emulsification/biodegradation (growth on crude oil as sole C-source)" and [106] is "Environmental tolerance testing (pH, salt and temperature)".

Figure 2:
Figure 2:
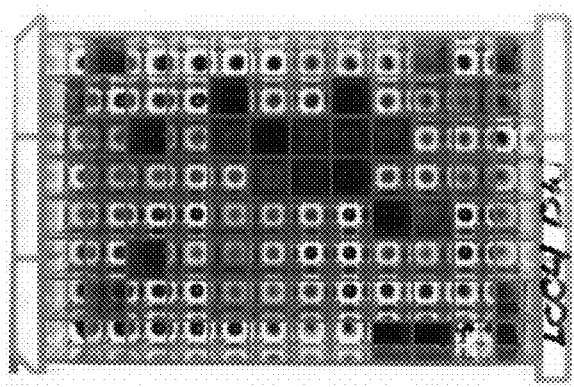

FIG. 2 shows a multi-well plate with a layer of heavy crude oil in each well and individual cultures of a strain library in each well. 2(a) shows a close-up of three individual wells (cultures) displaying various degrees of released oil, in the centre photo the oil appears completely dispersed (emulsified). 2(b) shows the entire plate with different strains displaying varying degree of changes in oil appearance (emulsification and degradation).

EXAMPLE 1

Typical Screening Method of the Invention

The BioTHOR culture collection (over 5000 isolates) was screened for the ability to emulsify or degrade heavy oil. Screening for the ability to grow on and disperse heavy oil was carried out in 96 deep well plates coated with a thin film of heavy oil. To the oil-coated well was added cultivation medium and inoculum. This screen used robots for pipetting, measuring optical density and cultivating at different temperatures. The plates were cultivated for some days and were inspected and photographed regularly (see FIG. 2).

524 isolates were selected based on ability to emulsify or degrade the oil. These isolates were then tested for tolerance to environmental change. 65-75% of the isolates can grow in the pH-range of 6-9, with an optimum of pH 6-7. With adaptation most of the isolates can grow at pH 5.5. Most of the isolates could grow at salt concentrations of up to 2.5% w/v and 30-50% w/v of the isolates were able to grow at salt concentration of 5.5% w/v The isolates grew from 40° C. to 60/70° C., with optimum temperature range of 50-60° C. Only a few isolates could grow at 80° C.

The 524 isolates were also screened against different heavy oils. They were also screened for alkane degradation activity. 165 strains were selected at this stage and were re-screened for emulsification and degradation of oil and alkane degradation. Alkane degradation was monitored by including nitroblue tetrazolium in the culture medium and measuring the development of a blue colouring in the culture medium. PAH (dibenzothiophene) degradation was monitored by measuring the development of a purple colouring in the culture medium.

Environmental tolerance tests (pH, salt concentrations, temperature) were performed. The number of isolates was then reduced to 47. During the final selection process the ability to emulsify and grow on heavy oil was emphasized over the ability to degrade alkanes. Isolates that scored poorly in the environmental tolerance tests were eliminated. 8 final isolates were then picked with 5 backups.

EXAMPLE 2

BLS Testing Protocols

Oil Displacement Assay

10 µl crude oil is added to the surface of 40 ml distilled water on a Petri dish and the allowed to spread out in a thin layer. 10 µl of the sample (e.g., culture or culture supernatant) is placed on the centre of the oil layer. BLS is present in the sample if the oil is displaced and a clear zone formed. The diameter of the clearing zone, measured after 30 seconds, will increase with the amount of BLS. Oil displacement may be measured as the displaced area.

Emulsification Capacity Index (E10).

This assay is described in more detail in Cooper, D. G. and Goldenberg, B. G. (1987), Surface-Active Agents from Two Bacillus Species, Appl Environ Microbiol 53(2): 224-229, and is based on the emulsification capacity of biosurfactants. Equal volumes of sample and a hydrocarbon (e.g., toluene or n-hexadecane) are added to a glass tube and vortexed at high speed for 2 minutes. After 10 minutes the emulsification index E10 is calculated as the ratio expressed as a percentage between the height of the emulsion layer and the total height of the sample hydrocarbon phase.

Shake Flask Test.

50 ml test samples are added to baffled 250 ml shake flasks containing 0.1 to 0.2 g crude oil. Flasks are incubated at 55° C. for 60 minutes on a rotary shaker (200 rpm). The qualities of the dispersed oil were evaluated visually.

Hydrocarbon Emulsification Test.

200 µl test sample is placed in a transparent 5 ml glass tube, 50 µl crude oil is added and vortexed for approximately 20 seconds. The quality of the formed emulsion is evaluated visually and scored from 0 (no emulsion) to 3 (oil-in-water emulsion stable for approximately 10 seconds).

The Drop Collapse Test.

This test was developed by Jain et al. (Jain, D. K., Collins-Thompson, D. L., Lee, H., and Trevors J. T. (1991), A drop-collapsing test for screening surfactant-producing microorganisms, J Microbiol Methods 13(4): 271-279)) and refined by among others Bodour and Miller-Maier (Bodour, A. A. and Miller-Maier R. M. (1998) Application of a modified drop-collapse technique for surfactant quantitation and screening of biosurfactant-producing microorganisms, J Microbiol Methods 32: 273-280).

The assay is performed in the lid of a 96-well plate. The lid has circular wells and crude oil (2 µl) is added to each of these wells and allowed to spread out and coat the well. The oil is allowed to equilibrate at room temperature overnight. Aliquots (5 µl) of sample are placed into the centre of the oil coated wells and the drop observed after 1 minute. If the drop remains beaded the test is scored as negative, if the drop collapses the result is scored positive. The test may be used qualitatively, it is however possible to score quantitatively by measuring the diameter of the drop after 1 minute.

The invention claimed is:

1. An automated method for selecting a microbial strain from within a microbial strain library which can degrade or emulsify a target oil substrate, said method comprising in no particular order, unless specified:
   (a) providing a plurality of receptacles adapted to receive a liquid microbial cell culture as part of a multi-well culture plate wherein the internal surface(s) of the receptacles are coated, at least in part, with a layer of the target oil substrate;
   (b) applying to each of said oil-coated receptacle a sample of one of the members of the strain library, wherein a plurality of members of the strain library are applied to the plate;
   (c) culturing said samples in a liquid cell culture medium and monitoring said oil layer coating at least part of the internal surface(s) of said receptacles for a change in its appearance, wherein a change in the appearance of said oil layer coating at least part of the internal surface(s) of said receptacles is indicative of degradation or emulsification of said target oil substrate;
   (d) selecting those samples from step (c) which caused degradation or emulsification of the oil substrate;
   (e) separately culturing either (i) all the members of the library applied in step (b) or (ii) the library members selected in step (d) in the presence of an n-alkane and monitoring for degradation of said n-alkane;

(f) separately culturing either (i) all the members of the library applied in step (b) or (ii) the library members selected in step (d) in the presence of a polycyclic aromatic hydrocarbon (PAH) and monitoring for degradation of said PAH;

(g) subjecting either (i) all the members of the library applied in step (b) or (ii) the library members selected in step (d) to environmental tolerance testing, wherein said testing comprises culturing the library members under varying environmental conditions and determining the limits of these conditions at which colony viability ceases, wherein said environmental conditions tested comprising temperature, pH and ionic concentration, and optionally further comprising $O_2$ concentration or pressure;

(h) optionally repeating steps (a) to (c) with the library members selected at step (d); and (i) selecting a microbial strain on the basis of its performance in steps (c), (e), (f), (g) and optionally (h).

2. The automated method of claim 1 wherein the microbial strain selected on the basis of its performance in steps (c), (e), (f), (g) and optionally (h) is a microbial strain which causes biodegradation or emulsification of the oil substrate, degradation of said n-alkane or said PAH and which tolerates environmental conditions selected from temperature, pH and ionic concentration, and optionally $O_2$ concentration or pressure that expected to be encountered during its use.

3. The automated method of claim 2 wherein each microbial strain of the library is scored in order of relative performance during steps (c), (e), (f), (g) and optionally (h) and selection is based on said scores.

4. The automated method of claim 3, wherein greater weight is given to the score for steps (c) and optionally (h) than steps (e), (f) or (g).

5. The automated method of claim 3 wherein the microbial strains of the library are ranked based on said scores and selection is of the portion of strains at the top of the rankings.

6. The automated method of claim 1, wherein said multi-well plate is a microplate.

7. The automated method of claim 1, wherein said oil is crude oil.

8. The automated method of claim 1, wherein said culturing in any one of steps (c), (e) or (f) is in a minimal medium.

9. The automated method of claim 1, wherein the n-alkane is a C16 or a $C_{32}$ alkane.

10. The automated method of claim 1, wherein the PAH is dibenzothiophene.

11. A method for preparing a microbial inoculum suitable for use to degrade or emulsify a target oil substrate, said method comprising
   (i) performing the automated method as defined in claim 1,
   (ii) culturing a sample of said selected strain to increase the numbers of cells in the culture.

12. A method of treating an oil reservoir or environmental remediation, said method comprising
   (i) performing the automated method as defined in claim 1, and
   (ii) introducing a sample of said selected microbial strain or said microbial inoculum to an oil reservoir or contacting a site or material undergoing environmental remediation with a sample of said selected microbial strain or said microbial inoculum.

13. A method for producing a biosurfactant-like substance (BLS), said method comprising
   (i) performing the automated method as defined in claim 1 and selecting a strain which can emulsify the target oil substrate,
   (ii) culturing a sample of said selected strain under conditions which result in BLS production.

14. A method of treating an oil reservoir or environmental remediation, said method comprising
   (i) the method for preparing a microbial inoculum as defined in claim 11, and
   (ii) introducing a sample of said selected microbial strain or said microbial inoculum to an oil reservoir or contacting a site or material undergoing environmental remediation with a sample of said selected microbial strain or said microbial inoculum.

* * * * *